United States Patent
Potyrailo et al.

(10) Patent No.: US 9,880,142 B2
(45) Date of Patent: Jan. 30, 2018

(54) PHOTONIC SENSOR FOR IN SITU SELECTIVE DETECTION OF COMPONENTS IN A FLUID

(71) Applicant: GENERAL ELECTRIC COMPANY, Schenectady, NY (US)

(72) Inventors: Radislav Alexandrovich Potyrailo, Niskayuna, NY (US); Wajdi Mohammad Ahmad, Edmond, OK (US); Nasr Alkadi, Oklahoma City, OK (US); John Andrew Westerheide, Edmond, OK (US); Glen Peter Koste, Niskayuna, NY (US); Sachin Narahari Dekate, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 15/155,748

(22) Filed: May 16, 2016

(65) Prior Publication Data

US 2016/0334327 A1    Nov. 17, 2016

Related U.S. Application Data

(60) Provisional application No. 62/162,156, filed on May 15, 2015.

(51) Int. Cl.
*G01N 21/00* (2006.01)
*G01N 33/18* (2006.01)
(Continued)

(52) U.S. Cl.
CPC ..... *G01N 33/1833* (2013.01); *G01N 21/7746* (2013.01); *G01N 21/783* (2013.01);
(Continued)

(58) Field of Classification Search
CPC ................ H01L 31/0481; H01L 31/05; H01L 31/02167; H01L 29/0665; G01N 21/41; G06F 17/50; B82Y 10/00
(Continued)

(56) References Cited

U.S. PATENT DOCUMENTS 4,708,941 A    11/1987 Giuliani
7,889,954 B2    2/2011 Sailor et al.
(Continued)

FOREIGN PATENT DOCUMENTS

CN    202275049 U    6/2012
WO    2014143045 A1    9/2014

OTHER PUBLICATIONS

Souteyrand et al., "Behaviour of cryptophane molecules in gas media", Sensors and Actuators B: Chemical, vol. 33, Issues: 1-3, pp. 182-187, Jul. 1996.
(Continued)

*Primary Examiner* — Tarifur Chowdhury
*Assistant Examiner* — Isiaka Akanbi
(74) *Attorney, Agent, or Firm* — Nitin N. Joshi

(57) ABSTRACT

A photonic sensor system includes: a photodetector; a signal processor coupled to the photodetector; and a sensor structure configured to provide fluid-response selectivity, spatially distribute light, and to receive light from a light source and convey light to the photodetector. The sensor structure includes a plurality of fluid sensitive interferometric nanostructure layers manufactured on a substrate; wherein the plurality of fluid sensitive interferometric nanostructure layers includes alternating high and low porosity layers.

27 Claims, 12 Drawing Sheets

(51) Int. Cl.
G01N 27/12 (2006.01)
G01N 21/77 (2006.01)
G01N 21/78 (2006.01)
G02B 6/02 (2006.01)
G02B 6/122 (2006.01)
G01N 33/00 (2006.01)
G01N 21/84 (2006.01)

(52) U.S. Cl.
CPC ....... G01N 27/125 (2013.01); G02B 6/02095 (2013.01); G02B 6/1225 (2013.01); *G01N 21/8483* (2013.01); *G01N 33/0047* (2013.01); *G01N 2021/7779* (2013.01); *G01N 2201/12* (2013.01)

(58) Field of Classification Search
USPC ................................ 356/437–438, 498, 450
See application file for complete search history.

(56) References Cited

U.S. PATENT DOCUMENTS

| | | | |
|---|---|---|---|
| 7,999,232 B2 | 8/2011 | Wilson et al. | |
| 8,076,617 B2 | 12/2011 | Norwood et al. | |
| 8,617,471 B2 | 12/2013 | Chakravarty et al. | |
| 2010/0002324 A1* | 1/2010 | Rozhin | B82Y 20/00 359/896 |
| 2012/0132930 A1* | 5/2012 | Young | H01L 31/0481 257/84 |
| 2012/0322164 A1* | 12/2012 | Lal | B82Y 10/00 436/501 |
| 2014/0106468 A1 | 4/2014 | Boersma | |
| 2015/0233818 A1* | 8/2015 | Manassen | G01N 21/41 356/369 |

OTHER PUBLICATIONS

Benounis et al., "Study of a new evanescent wave optical fibre sensor for methane detection based on cryptophane molecules", Sensors and Actuators B: Chemical, vol. 107, Issues: 1, pp. 32-39, 27 May 2005.
Gayraud N et al., "Mid-Infrared Methane Sensing Using a Silica Photonic Bandgap Fiber", Lasers and Electro-Optics, 2007 and the International Quantum Electronics Conference. CLEOE-IQEC 2007. European Conference on, pp. 1, Jun. 17-22, 2007, Munich.
Michael J. Sailor, "Color me sensitive: Amplification and discrimination in photonic silicon nanostructures", ACS Nano, 1(4), pp. 248-252, 2007.
Pablo A. Denis, "Methane adsorption inside and outside pristine and N-doped single wall carbon nanotubes", Chemical Physics, 353, pp. 79-86, 2008.
Wu et al., "High-capacity methane storage in metal-organic frameworks M2(dhtp): The important role of open metal sites", Journal of American Chemical Society, 131, pp. 4995-5000, 2009.
Xi-Jun et al., "Application research of hollow-core photonic crystal fibers in methane sensing system", Intelligent Control and Automation (WCICA), 2010 8th World Congress on, pp. 811-815, Jul. 7-9, 2010, Jinan.
Little et al,, "Synthesis and methane-binding properties of disulfide-linked cryptophane-0.0.0"v, Angewandte Chemie International Edition, vol. 51, Issue 3, pp. 764-766, Jan. 16, 2012.
Zhao et al., "Bio-inspired variable structural color materials", Chemical Society Reviews, 41(8) , pp. 3297-3331, Apr. 21, 2012.
Khoshaman et al., ".High sensitivity, supramolecular thin films for sensing of methane", Sensors, 2012 IEEE, pp. 1-4, Oct. 28-31, 2012, Taipei.
Zeitler et al., "Grand canonical monte carlo simulation of low-pressure methane adsorption in nanoporous framework materials for sensing applications", Journal of Physical Chemistry C , 116 (5), pp. 3492-3502, 2012.
Luchansky et al., "High-Q optical sensors for chemical and biological analysis", Analytical Chemistry, 84(2), pp. 793-821, 2012.
Wang et al., "A room temperature SAW based methane gas sensors", Ultrasonics Symposium (IUS), 2013 IEEE International, pp. 2148-2150, Jul. 21-25, 2013, Prague.
Askim et al., "Optical sensor arrays for chemical sensing: The optoelectronic nose", Chemical Society Reviews, 42, pp. 8649-8682, 2013.
Potyrailo et al., "Bionanomaterials and bioinspired nanostructures for selective vapor sensing", Annual Review of Materials Research, vol. 43, pp. 307-334, 2013.
Xu et al., "Photonic crystal for gas sensing", Journal of Materials Chemistry C,1, pp. 6087-6098, 2013.
Burgess et al., "Structural colour in colourimetric sensors and indicators", Journal of Materials Chemistry C, 1, pp. 6075-6086, 2013.
Pacholski et al., "Photonic crystal sensors based on porous silicon", Sensors 2013, 13(4), pp. 4694-4713, 2013.
Potyrailo, R.A. et al., "Discovery of the surface polarity gradient on iridescent Morpho butterfly scales reveals a mechanism of their selective vapor response", Proc. Natl. Acad. Sci. U.S.A. 110(39),15567-15572, 2013.
Fenzl et al., "Photonic crystals for chemical sensing and biosensing", Angewandte Chemistry International Edition, vol. 53, Issue:13, pp. 3318-3335, Mar. 24, 2014.
Chan et al., "Optical detection of C2 hydrocarbons ethane, ethylene, and acetylene with a photonic crystal made from carbonized porous silicon", Inorganica Chimica Acta, vol. 422, pp. 21-29, Oct. 1, 2014.
Farid A. Harraz, "Porous silicon chemical sensors and biosensors: A review", Sensors and Actuators B: Chemical, vol. 202, pp. 897-912, Oct. 31, 2014.
Wang et al., Responsive photonic crystal for the sensing of environmental pollutants, Trends in Environmental Analytical Chemistry, vol. 3-4, pp. 1-6, Nov. 2014.
Yetisen et al., "Holographic sensors: Three-dimensional analyte-sensitive nanostructures and their applications", Chemical Reviews,114(20), pp. 10654-10696, 2014.
Baker et al., "Two-dimensional photonic crystals for sensitive microscale chemical and biochemical sensing", Lab on a Chip,15(4), 971-990, Feb. 21, 2015.
Zhang et al., "Measurement of methane concentration with cryptophane E infiltrated photonic crystal microcavity", Sensors and Actuators B: Chemical, vol. 209, pp. 431-437, Mar. 31, 2015.
Potyrailo, R.A. et al., "Towards Outperforming Conventional Sensor Arrays with Fabricated Individual Photonic Vapour Sensors Inspired by Morpho Butterflies," Nature Communications vol. 6, pp. 1-12, ISSN (online) 2041-1723, Sep. 1, 2015.
Potyrailo, R.A. et al., Detection of Individual Vapors and Their Mixtures Using a Selectivity-Tunable Three-Dimensional Network of Plasmonic Nanoparticles, Angewandte Communications, Chemical International Ed., 2013, vol. 52, pp. 10360-10364.
Potyrailo, R.A. et al.. "Use of the Original Silicone Cladding of an Optical Fiber as a Reagent-Immobilization Medium for Intrinsic Chemical Sensors," Fresenius' J. Anal. Chemical,1999, vol. 364, pp. 32-40, Nov. 1998.
Wang T. et al, A Long Period Grating Optical Fiber Sensor with Nano-Assembled Porphyrin Layers for Detecting Ammonia Gas, Sensors and Actuators B: Chemical 2016, vol. 228, pp. 573-580.

\* cited by examiner

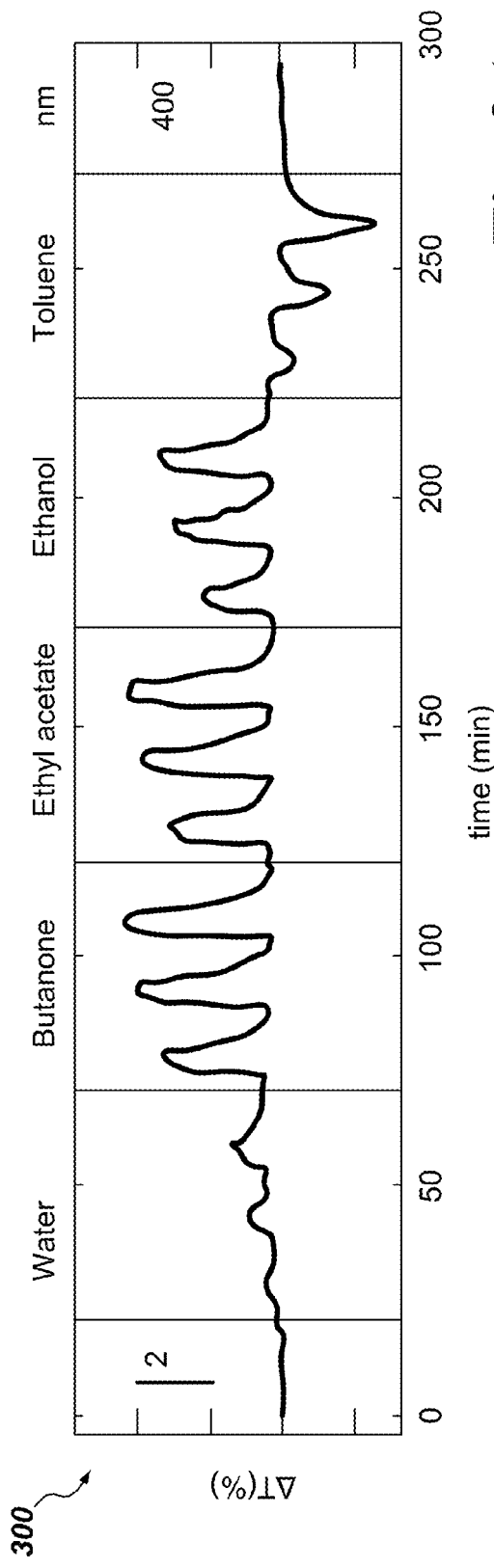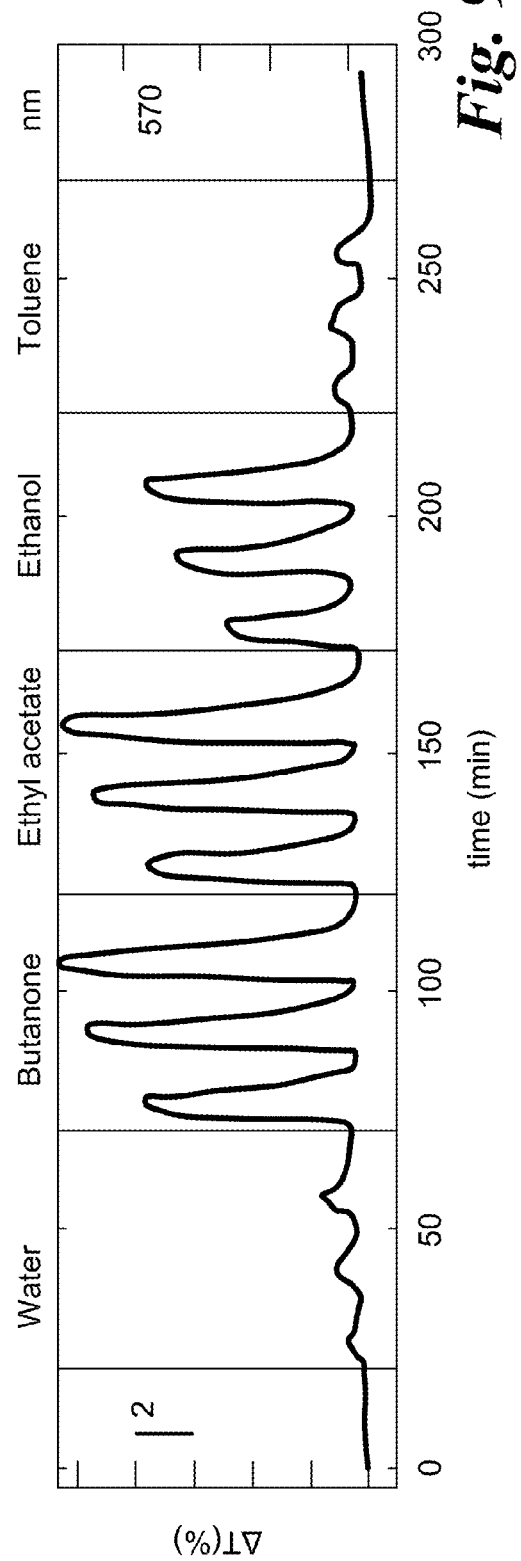

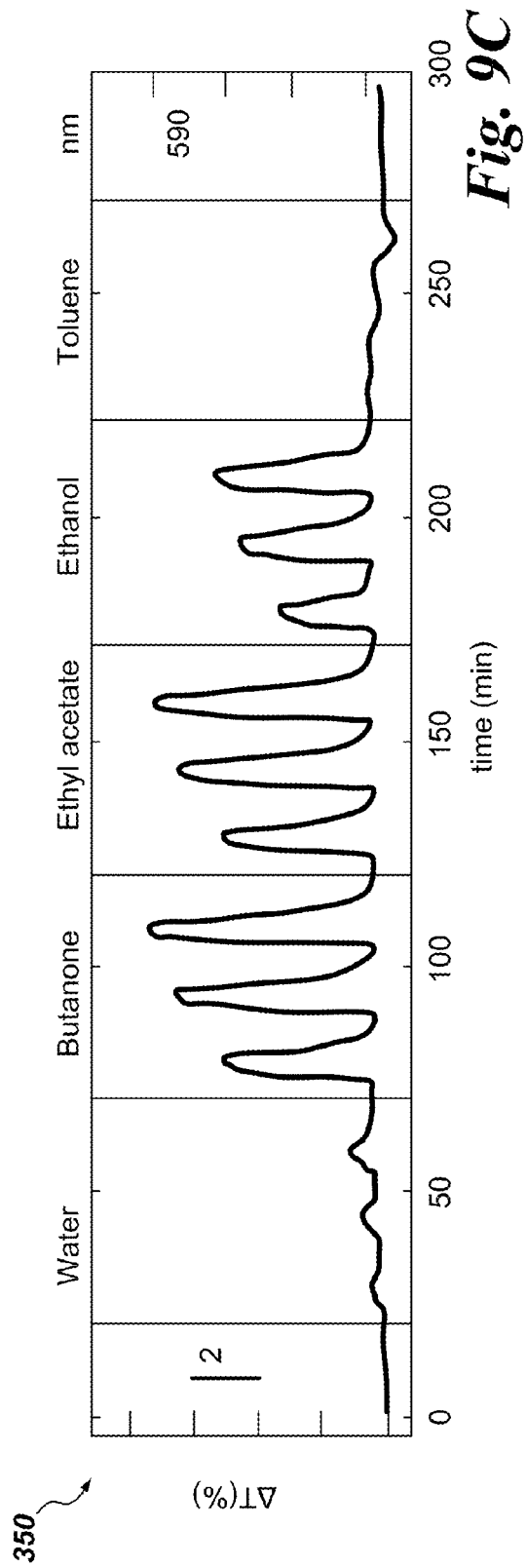
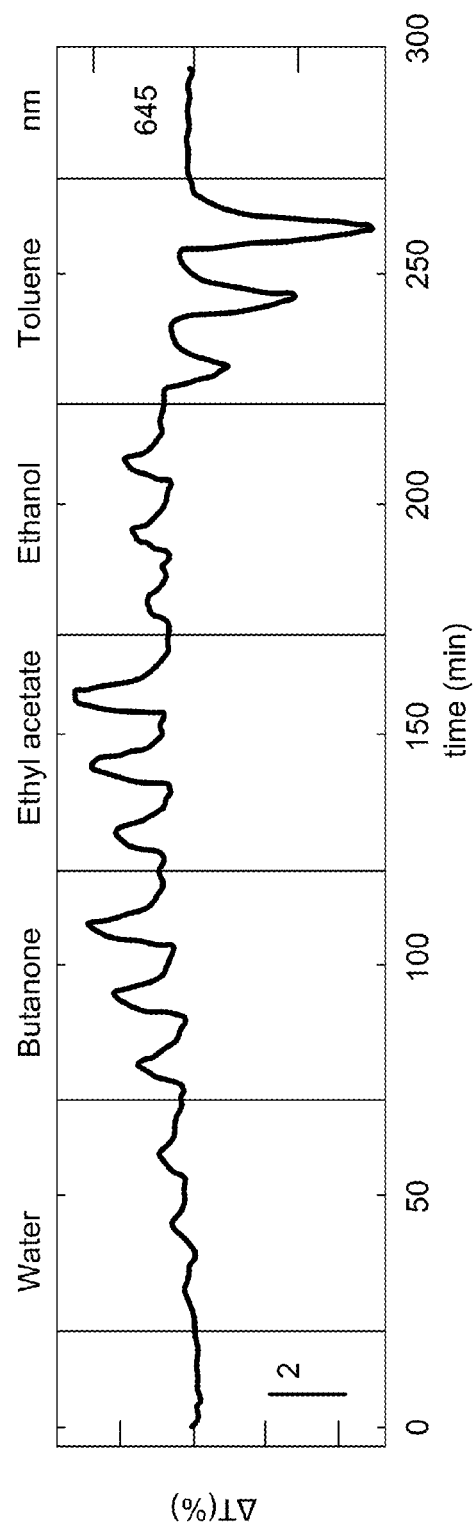
Fig. 9C
Fig. 9D

PHOTONIC SENSOR FOR IN SITU SELECTIVE DETECTION OF COMPONENTS IN A FLUID

CROSS-REFERENCE TO RELATED APPLICATIONS

This application claims priority to, commonly assigned, U.S. Application Ser. No. 62/162,156, Entitled: STRUCTURAL COLOR-BASED SENSORS FOR IN SITU SELECTIVE DETECTION OF METHANE. The contents of which are incorporated herein by reference in its entirety.

BACKGROUND

The subject matter of this disclosure relates generally to sensing and, more particularly, to photonic sensors for in situ selective detection of components in fluids, such as methane in an industrial fluid.

Colorimetric gas sensing is a well-established methodology known for almost a century. In colorimetric gas sensing, there are diverse forms of colorimetric sensing materials such as sensing films, sensing tapes, sensing chips, sensing fibers, and others. These and other colorimetric sensing materials operate on two different basic principles.

The first principle involves chemical means of color formation by chemical dyes, pigments, polymers, and other chemicals where the color is produced due to the specific chemical structure of the material. The color change of the sensing material is further induced by a certain gas upon interaction of this gas and the sensing material where the interaction ranges from weak to strong interaction forces. The classification and strengths of interactions between molecules of a gas and molecules of the sensing material are well established and range from weak to strong interactions. Non-limiting examples of such interactions include covalent or ionic bond formation, ligand coordination, electrostatic ion-ion and proton acid-base interactions, hydrogen bonding, halogen bonding, charge-transfer and $\pi$-$\pi$ molecular complexation, dipolar and multipolar interactions, and van der Waals interactions (e.g., physical adsorption). This principle of chemical means of color formation for gas detection is well established. Attractive features include (1) availability of different known chemistries for different gases and (2) known fabrication methods of such colorimetric sensors. However, serious limitations of such sensors include inability to measure some simple small molecule gases for which there are no chemical interactions available.

The second principle involves chemical means of color formation by physical principles of light interactions with optical materials and involves light interference, diffraction, scattering, and combinations thereof. Known photonic resonant vapor sensors operate on univariate vapor quantitation principles based either on the detection of wavelength shift of the resonance peak or change in signal intensity. These sensors are based on porous silicon, self-assembled colloidal particles, mesoporous photonic crystals, inverse opals as well as high-Q resonators. These types of sensors have been demonstrated for different gases, including hydrocarbon gases such as methane, ethane and others. The significant limitation of photonic resonant vapor sensors that operate on univariate vapor quantitation principles is in their cross-sensitivity to other gases in atmosphere. Such cross-sensitivity reduces accuracy of gas detection and increases the likelihood of false alarms that are unacceptable in demanding applications such as in situ detection of methane leaks in various equipment types e.g. gate and compressor stations, machine halls, valves, pressure relief valves, connectors, flanges, and others as well as along the pipelines.

Fugitive methane detection is gaining strong attention in the industrial arena. This is primarily driven by growing regulatory measures to mitigate these emissions for environmental protection and also gas monetization. However, mitigation is driven by detection. Across the economy, there are multiple sectors in which methane emissions can be reduced, from coal mines and landfills to agriculture and oil and gas development. For example, in the agricultural sector, over the last three years, the Environmental Protection Agency (EPA) and the Department of Agriculture have worked with the dairy industry to increase the adoption of methane digesters through loans, incentives, and other assistance. In addition, when it comes to the oil and gas sector, reducing emissions and enhancing economic productivity are becoming quite important. For example, work is underway to advance the production of oil and gas in the Bakken while helping to reduce venting and flaring.

Based on EPA studies, methane emissions accounted for nearly 10 percent of U.S. greenhouse gas emissions in 2012, of which nearly 30 percent came from the production, transmission and distribution of oil and natural gas. EPA found that main emission sources in Oil and Gas operations included gate and compressor stations, machine halls, gate valves, pressure relief valves, control valves, connectors, flanges, casing, wellheads and others as well as along the pipelines networks especially where pipe meets and forms a connection. These sources of emissions are projected to rise more than 25 percent by 2025 without additional steps to lower them. Reducing methane emissions means capturing valuable fuel that is otherwise wasted and reducing other harmful pollutants—a win for public health and the economy. Achieving the Administration's goal would save up to 180 billion cubic feet of natural gas in 2025, enough to heat more than 2 million homes for a year. For these reasons, a strategy for cutting methane emissions from the oil and gas sector is an important component of efforts to address climate change. As part of this strategy, methane detection is considered as the cornerstone to reduce emissions from oil and gas sector. Methane Detection technologies have to be cost effective, reliable, and safe for the oil and gas customers to adopt, use, and rely on.

While there are many commercially available sensors that detect methane and other fluids, there remain long felt needs including, but are not limited to: visual-indicator and machine-indicator-sensors that are intrinsically safe, require little or no power, high-sensitivity, high-selectivity, without high-temperature heating for catalytic reactions, that also offer low cost and technical simplicity for cost-effective detection and visualization of fluids, including methane.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In accordance with an aspect of the present invention, a fluid sensor comprises: a plurality of fluid sensitive interferometric nanostructure layers configured in an open-fluid resonant structure. An open-fluid structure allows a measured fluid to interact with its regions. An open-fluid structure may comprise an open-air structure or an open-liquid structure.

In accordance with another aspect of the present invention, a fluid sensor comprises: a plurality of fluid sensitive interferometric nanostructure layers defining an open-fluid resonant structure; and a polarization sensitive photodetector configured to detect optical contributions of different components of a fluid to the open-fluid resonant structure.

In accordance with another aspect of the present invention, a photonic sensor system comprises: a photodetector; a signal processor communicatively coupled to the photodetector; and a sensor structure configured to provide fluid-response selectivity, spatially distribute light, and to receive light from a light source and convey light to the photodetector.

In accordance with an aspect of the present invention, a method of selective measurement of a plurality of components in a fluid in a process area comprises: exposing a sensing structure to the fluid; interrogating the sensing structure with light from a light source, wherein the light source is outside the process area and the light has a set of predetermined properties; measuring a change in optical properties of the sensing structure; correlating the measured change to a stored value; and providing quantitative values of levels of the plurality of components in the fluid.

In one embodiment, a methane detection system described herein comprises a single sensor for selective detection of methane, where the sensor is comprised of a multivariable photonic resonant transducer with an open-air structure to allow ambient environment to interact with the sensor, and a methane-sensing moiety integrated as a part of the photonic impermeable resonant transducer such that the sensor exhibits selective vapor response involving spatially-controlled interactions of different gases with the multivariable photonic resonant transducer.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIGS. 7-9 collectively illustrate experimental verification of the operation of an embodiment of the photonic sensor from FIG. 5, and specifically:

FIG. 7 illustrates transmission spectrum of the optical fiber with the Nile Red reagent impregnated in the cladding as used herein;

FIG. 8 illustrates the results of the principal components analysis (PCA) of the spectral responses of the photonic sensor as measured across the spectral response form about 350 nm to about 900 nm;

FIGS. 9A-9D illustrate the response of multivariable photonic sensor at four representative wavelengths (e.g., 400 nm, 570 nm, 590 nm, 645 nm), respectively;

FIG. 10 illustrates the emission spectrum of the super continuum light source as used herein.

FIG. 11 illustrates the emission spectrum of the super continuum light source as transmitted through the optical fiber and the long period grating on the sensing region of the fiber as used herein.

FIG. 12 illustrates the results of measurements of thermal effects on the optical fiber within the sensing region (S) that is the long period grating and the fiber link (L) as used herein.

DETAILED DESCRIPTION

Figure 1:
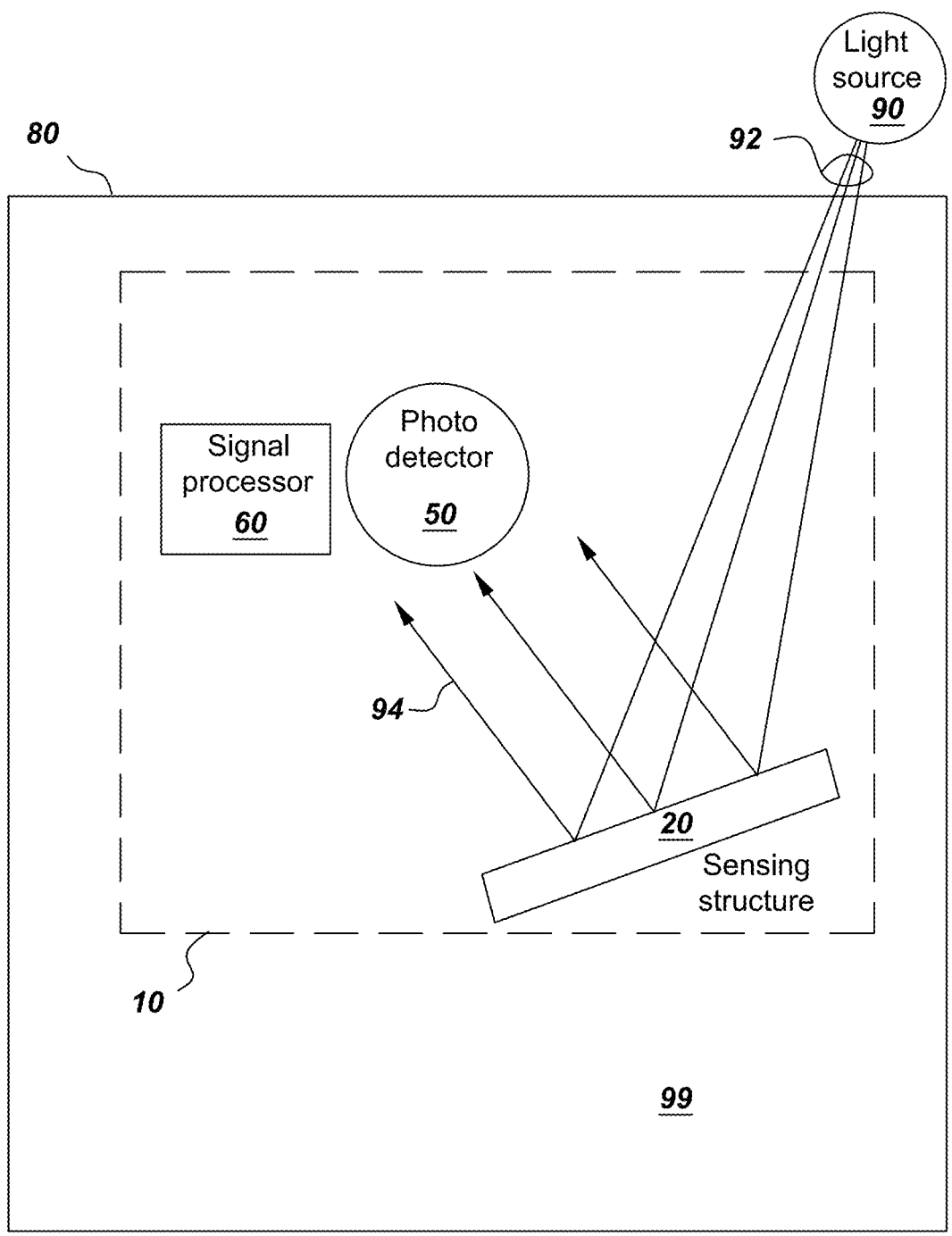
FIG. 1 illustrates a schematic diagram of a photonic sensor system in accordance with an embodiment.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The term "fluid" as used herein includes gases, vapors, liquids, and emulsions that include industrial, non-industrial, and/or naturally occurring fluids. Fluids may include naturally occurring fluids such as air, water, oils, body fluids, biological fluids, and the like that occur in natural living and non-living systems.

The term "industrial fluid" as used herein includes fluids that typically may be used on an industrial site or structure. Industrial fluid includes ambient air on an industrial site or structure, compressed air, exhaled air, inhaled air, fugitive emission, biogenic emission, thermogenic emission, pollution, air pollution, water pollution, oil pollution, natural gas, water, naturally occurring fluid, synthetic fluid, lubricant, fuel, hydraulic media, drive fluid, power steering fluid, solvent, power brake fluid, drilling fluid, oil, crude oil, heat transfer fluid, insulating fluid, and the like.

The terms "industrial site" or "industrial structure" or "process area" as used herein includes a naturally occurring site or structure that is used for industrial applications or an artificial site or structure produced by any industry or industrial company that is used for industrial, environmental, recreational, residential, military, security, heath, sports and other applications. Non-limiting examples of an industrial site include manufacturing facility, processing facility, disposal facility, industrial research facility, gas producing facility, oil producing facility, residential facility, sports facility, military facility, security facility, and others. In an aspect, the condition of the industrial site is based on the concentration of the external contaminant in the industrial fluid. Non-limiting examples of external contaminants include methane, ethane, hydrocarbon, ethylene, acetylene, and water.

The term "analyte" as used herein includes any substance or chemical constituent that is the subject of a quantitative chemical analysis. Non-limiting examples of an analyte include methane, ethane, hydrocarbon, ethylene, acetylene, water, fuel, hydrogen, carbon monoxide, carbon dioxide, metals, aging products, or any combination thereof. In certain embodiments, the sensing materials of the present disclosure may be configured to detect analytes.

The term "interferent" as used herein includes any substance or chemical constituent that undesirably affects quality of measurements of the analyte by reducing the accuracy, precision, or other known parameters of measurements of the analyte. Non-limiting examples of interferents and ambient environmental noise contributors include temperature and the presence of interferents in a fluid. Filters (physical, chemical, and/or electronic) may be used, based on the application specific parameter to reduce, eliminate, or account for the presence and/or concentration of such interferents.

The term "multivariable sensor" as used herein refers to a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" as used herein refers to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "sensing materials" and "sensing films" as used herein includes, but is not limited to, materials deposited onto a photonic sensor, to perform the function of predictably and reproducibly affecting the resonant sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art. Suitable sensing materials include polymer, organic, inorganic, biological, composite, and nano-composite films that change their optical property based on the environment in which they may be placed. A sensing material may be applied onto the optical sensor. Non-limiting examples of sensing materials include cryptophanes, zeolites, metal-organic frameworks, cage compounds, clathrates, inclusion compounds, semiconducting materials, metal oxides, electrospun polymer nanofibers, electrospun inorganic nanofibers, nanotubes, nanosheets, electrospun composite nanofibers, and other sensor materials selected based on application specific parameters.

Embodiments described herein provide a technical solution for the selective detection of methane using colorimetric sensors based on physical principles of light interactions with an optical methane-sensitive or other fluid-sensitive material. This methane-sensitive material is fabricated to produce structural color based on the nanoscale features of the material and to predictably change the color as a function of methane concentration. This sensor provides rejection of ambient gaseous interferents by its four design features such as geometrical design, functionalization design, spatial distribution of functionalization design, and spatial distribution of light of the structure design, and its optical readout.

In an embodiment, measurements of properties of fluids may be performed to determine dynamic signatures of the changes of chemical constituents in the fluid. The time scales of these dynamic signatures may vary greatly. Suitable timescale in a range of from about 0.01 second to about 200 days may be useful to determine different dynamic processes in industrial sites. Such determinations allow the identification of dynamic signatures of the leaks on industrial site, relation of the identified signature with the known leak signature from a specific industrial site component, and determination of the location of the leak based on the signature.

Measurements of properties of fluids may be performed at extreme temperature conditions. Depending on the application, these conditions may range from temperatures down to about −260 degrees Celsius and to temperatures up to about +1600 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +1600 degrees Celsius may be useful in monitoring equipment where the temperature of operating components of the equipment can reach about +1600 degrees Celsius. Examples of equipment that operates at about 250 degrees Celsius may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer. Examples of equipment that operates at about 1000 and up to 1500 degrees Celsius include gas turbines. Examples of equipment that operates at about 1600 degrees Celsius include aircraft jet engines.

In accordance with embodiments, a photonic sensor comprises a sensing structure design that involves control of selectivity by four means such as geometrical design, functionalization design, spatial distribution of functionalization design, and spatial distribution of light in the structure design.

The geometrical design involves interaction of illumination light with different portions of the structure and generation of optical spectral features that are associated with different spatial regions of the sensing structure. For example, in a multilayer interference sensing structure, different spacing (air gap) between the individual layers and their thickness result in different interference colors produced from the same sensing structure.

The functionalization design involves a chemical, biological, physical, or composite material of the sensing structure to provide a desired response to analyte vapor or vapors. For example, the sensing structure is made from polymeric, chemical, biological, physical, or composite material that is chosen to interact with fluids or the sensing structure is made from an inert material that is further coated with polymeric, chemical, biological, physical, or composite material that is chosen to interact with fluids.

The spatial distribution of functionalization design involves diverse functionalization of different spatial regions of the sensing structure. For example, the spatial distribution of functionalization is a step or gradient distribution in functionality of the sensing structure within the propagation region of light within the sensing structure.

The spatial distribution of light in the sensing structure design involves illumination of the sensing structure with a defined input lightwave profile and creation of predetermined light pattern within the structure that is different from the input illumination lightwave profile. Non-limiting examples of the effects on the input lightwave profile include light polarization, light scatter, light attenuation, light absorption, light refraction that are produced within the sensing structure.

Thus, when the geometrical design involves interaction of illumination light with different portions of the structure, which is functionalized in a step or gradient distribution fashion, optical spectral features are generated that are associated with different spatial regions of the sensing structure. These different optical spectral features are termed as "spectrally multiplexed" from different spatial regions of the structure. Similarly, if different optical polarization features are produced from different spatial regions of the structure, these features are termed as "polarization multiplexed". Similarly, if different optical time-domain (for example, luminescence lifetime) features are produced from different spatial regions of the structure, these features are termed as "time-domain multiplexed".

The use of such spectral multiplexing, polarization multiplexing, or time-domain multiplexing may allow to expand the dynamic range of measurements where the sensitivity of response of the structure to the fluid component of interest is different for different spectral positions (wavelengths), polarization angles, or time-domain delays. These different sensitivities allow their linear, quadratic, or other functional combination to achieve a broader or expanded dynamic range of measurements of the concentration of the fluid component of interest.

Different effects on the interactions of optical radiation with the sensing region in the disclosed multivariable sensor may be described by the matrix algebra where exemplary individual matrix inputs may include light source properties (such as intensity, wavelength spectral profile, polarization, spatial coherence, temporal coherence, temporal response), sensing structure geometry (such as resulting in waveguiding geometry, multi-mode waveguiding geometry, few-mode waveguiding geometry, single-mode waveguiding geometry, interference geometry, multilayer interference geometry, diffraction geometry, single-ring resonator geometry, multi-ring resonator geometry, whispering-gallery wave geometry, combined geometry), sensing structure functionalization, spatial distribution of sensing structure functionalization, spatial distribution of light in sensing structure, detector properties, and other properties that mathematically describe the multivariable sensor shown as:

$$\begin{bmatrix} \text{Light} \\ \text{source} \\ \text{properties} \end{bmatrix} * \begin{bmatrix} \text{Sensing} \\ \text{structure} \\ \text{geometry} \end{bmatrix} * \begin{bmatrix} \text{Sensing} \\ \text{structure} \\ \text{functionalization} \end{bmatrix} * \begin{bmatrix} \text{Spatial} \\ \text{distribution of} \\ \text{functionalization} \end{bmatrix} *$$

$$\begin{bmatrix} \text{Spatial} \\ \text{distribution of} \\ \text{light in structure} \end{bmatrix} * \begin{bmatrix} \text{Detector} \\ \text{properties} \end{bmatrix} = \begin{bmatrix} \text{Photonic} \\ \text{multivariable} \\ \text{sensor} \end{bmatrix}$$

Other components of the matrix algebra description of the multivariable sensor may include aging, spatial distribution of aging of the sensing region, light source stability, detector stability, and others.

The matrix algebra presentation of this sensor and its sensing region may provide the ability to design the sensing region with reduced or eliminated effects from interferents. For example, in the matrix algebra form, the detected response of the sensor may be presented as the quantifiable response to analyte 1 and analyte 2 and a suppressed response to interferent 1 and interferent 2. To achieve this goal, the analytes such as analyte 1 and analyte 2 and interferents such as interferent 1 and interferent 2 are considered in their matrix representation with a multivariable photonic sensor. Such sensor may be designed to meet the response criteria shown as:

$$\begin{bmatrix} \text{Photonic} \\ \text{multivariable} \\ \text{sensor} \end{bmatrix} * \begin{bmatrix} \text{Analyte 1} \\ \text{Analyte 2} \\ \text{Interferent 1} \\ \text{Interferent 2} \end{bmatrix} \rightleftarrows \begin{bmatrix} [\text{Analyte 1}] \\ [\text{Analyte 2}] \\ 0 \\ 0 \end{bmatrix}$$

Sensor     Industrial site     Rejection of undesired effects

Referring to FIG. 1, a schematic diagram depicts an exemplary photonic sensor system in accordance with aspects of the present invention. The system 10 includes a sensing structure 20, a photo detector 50 and a signal processor 60, collectively operating in a process area 80. A light source 90 operates outside the process area 80, wherein resides a fluid 99. Incident light 92 from the light source 90 impinges on the sensing structure 20 and then reflects 94 to the photo detector 50.

In an embodiment, a sensing structure can comprise a photonic sensor that is positioned within an industrial site (process area) and is illuminated with a natural light source (e.g., the Sun, the scatter from the sky, the Moon). The sensor may be in a form of a flat sheet of a size from about 1 mm to about 500 mm and manufactured on a rigid, flexible, or stretchable substrate. In an embodiment, the sensor readout may be performed by visual inspection such as manual inspection by observing the color of the sensor in the visible range of the optical spectrum. In another embodiment the sensor readout may be performed by machine inspection such as automated or unattended inspection by observing the optical response of the sensor in the ultraviolet, visible near-infrared, infrared, and/or far-infrared range of the optical spectrum. Visual or machine inspection may be performed by the human or machine operator positioned on a ground or airborne. Non-limiting examples of positions on the ground include standing, walking, or driving. Non-limiting examples of airborne positions including flying, flying by a fixed wing platform, or flying by an air-drone platform. Non-limiting examples of machine inspection include inspection by robots drones, unmanned vessels, and unmanned vehicles. Non-limiting examples of drones include airborne, ground-based, and subsea drones. The sensor readout may be performed in a stand-off detection mode from a distance between the sensor and the detector that ranges from about 1 cm to about 10 km. The stand-off detection involves an open path of the detected light between the sensor and the detector. In an embodiment, the industrial site is a site along a gas or oil pipeline, gas or oil production site, gas or oil distribution site, and/or gas or oil transport site.

In one embodiment, the sensor system has a detector which is within the process area while the light source is outside the process area. The detection may be on a movable platform such as ground-based or air-based platform, while the light source is essentially stationary during the period of time of measurements and spatially separated from the sensor system. This spatial separation can be in the range from 10 meters to the distance to the Sun which is about 150 million kilometers from the Earth.

In one embodiment, at least one optical property of the sensor system is changing upon exposure to an industrial fluid and upon illumination with a light source that has a predetermined illumination lightwave profile.

In one embodiment, the sensors imbedded into pipeline markers, which are deployed every several tens of meters along buried pipelines at prominent points along the route. The illumination and detection system may be mounted to a manned or unmanned aerial vehicle which may fly along the route, measuring each marker to determine if there is any gas escaping and exposing the sensor. Alternatively, the illumination is provided by the natural light source (the Sun, sky, the Moon) while the detection system may be mounted to a manned or unmanned aerial vehicle which may fly along the route, measuring each marker to determine if there is any gas escaping and exposing the sensor.

In one embodiment, the sensor may contain a pigment which has its multivariable response in the presence of the gas. In one embodiment, the sensor may produce a reversible response upon exposure to a fluid. In one embodiment, the sensor may produce a non-reversible response upon exposure to a fluid.

Figure 2A:
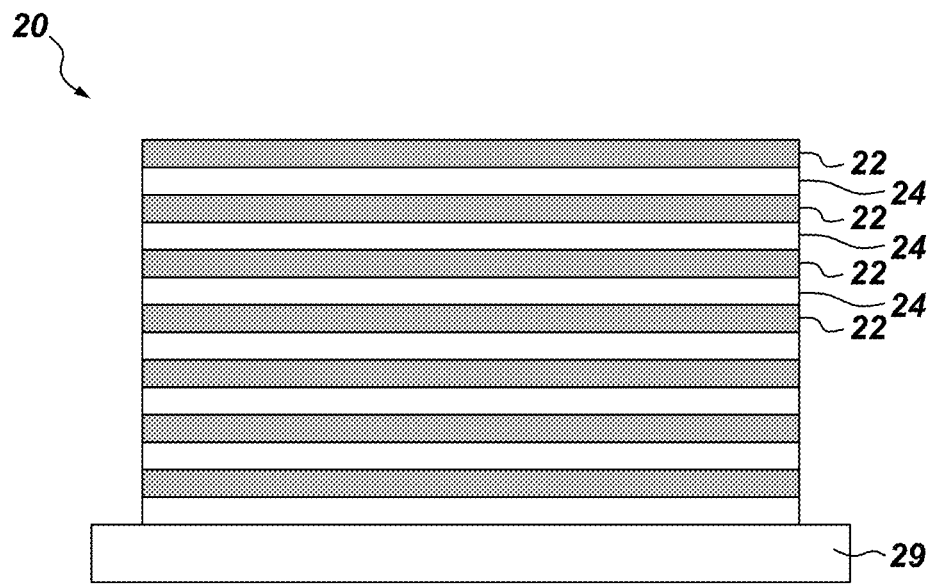
FIGS. 2A and 2B illustrate multilayer interferometric nanostructures in accordance with embodiments.
Figure 2B:
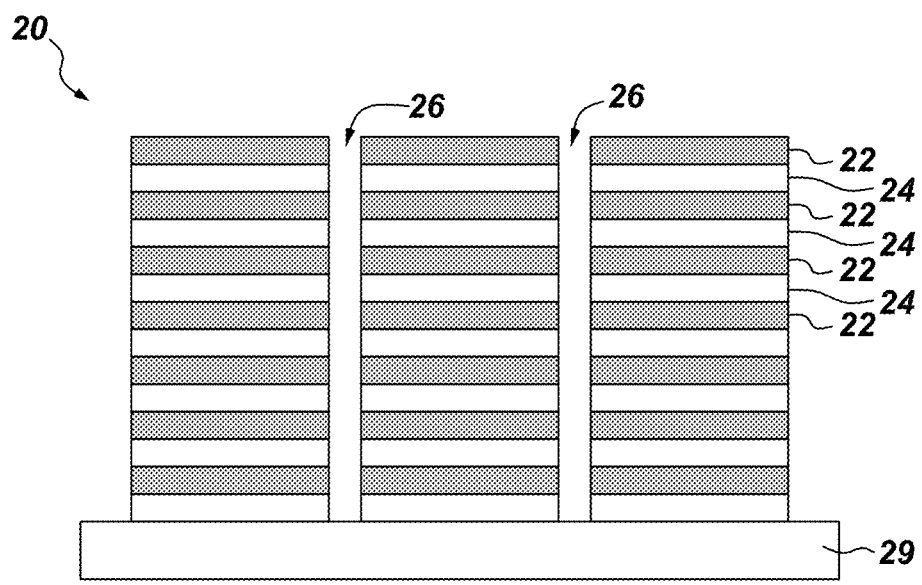

In some embodiments, the resonant structure 20 is a multilayer interferometric nanostructure as illustrated in FIGS. 2A and 2B. The nanostructure may be fabricated by using techniques generally known in the art to fabricate nanoscale structures. In one embodiment, alternating layers 22, 24 of at least two types of materials having different refractive indices may be deposited. Deposition of materials can be accomplished using spin coating, vapor deposition, sputtering or any other known methods. In another embodiment, fabrication of the nanostructure may be accomplished through anodization of silicon at different conditions to form alternating high and low porosity layers and producing a porous silicon resonator. For example, high porosity layers can be obtained with a relatively high current density (e.g. 50 mA/cm$^2$) for a relatively short period of time (e.g., approximately 5 seconds). Low porosity layers can be obtained with a relatively low current density (e.g., 5 mA/cm$^2$) for a relatively long period of time (e.g., approximately 20 seconds). In the fabricated multilayer interferometric nanostructure of FIG. 2A, the thicknesses of the layers 22, 24 may be the same or vary through the bulk. Having the same or very similar thicknesses of each layer provide a more narrow spectral response (e.g. reflectance). Different thicknesses of each layer provide a more diverse spectral response that is attractive for selective gas sensing. Reactive ion etching (RIE) can be further applied to form spacers 26 there through to produce individual, relatively narrow, multilayer interferometric nanostructures 20 as shown in FIG. 2B. Non-limiting examples of refractive index values for the resonant multilayer interferometric nanostructures described herein may range from 1.01 to 5, where the contrast between n1 and n2 can be in the range from 0.00001 to 5. Non-limiting examples of thickness of individual layers may be from 10 nm to 10,000 nm.

Figure 3:
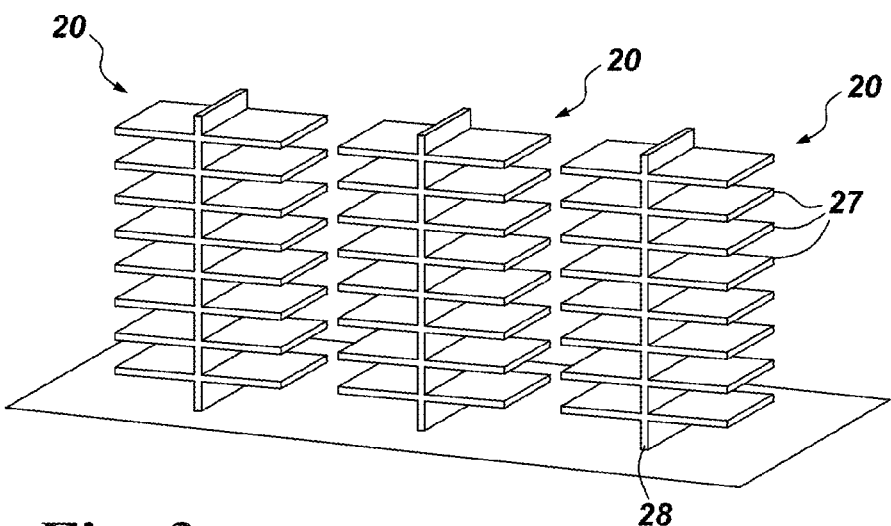
FIG. 3 illustrates multilayer interferometric nanostructures with short lengths of individual horizontal lamella that are supported in the middle by a vertical ridge in accordance with one embodiment.

In another embodiment, resonant multilayer structure 20 may be a multilayer interferometric nanostructure with short lengths of individual horizontal lamella 27 that are supported in the middle by a vertical ridge 28 as shown in FIG. 3. The periodic arrangement of these individual "tree" nanostructures 20 also adds diffraction effects to the sensor response. The variation of spacing between the individual multilayer interferometric nanostructures 20 controls the quality factor of the resonance and leads to a relatively high quality factor of the resonance at small spacing between individual multilayer interferometric nanostructures. As shown in FIG. 3, the width of the nanostructure 20 may be in the range from 10 nm to 100 um, while the spacing between individual multilayer interferometric nanostructures may be in the range from 1 nm to 100 um.

In yet another embodiment, the resonator structure used to promote enhanced gas response is a photonic crystal fiber resonator. Such a fiber has the ability to confine light in its hollow core. In photonic crystal fibers, light is guided by structural modifications, and not only by refractive index differences in the fiber.

Figure 4A:
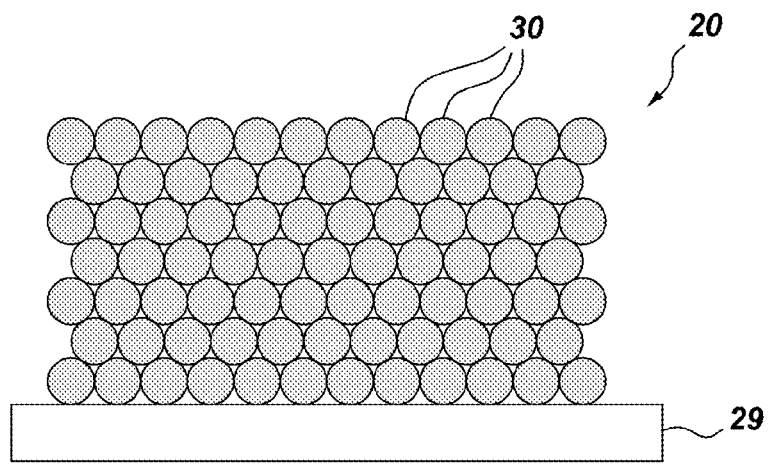
FIGS. 4A and 4B illustrate, respectively, a self-assembled photonic crystal colloidal particles arrays resonator and an inverse opal resonator in accordance with embodiments.
Figure 4B:
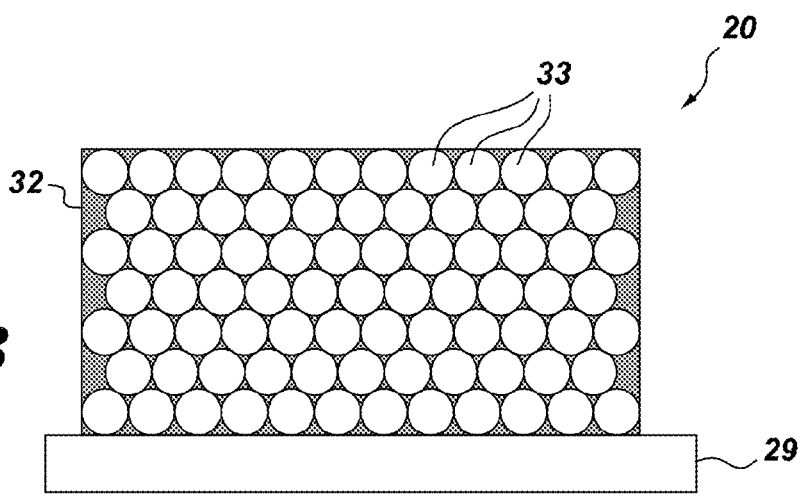

In another embodiment, this resonator structure 20 used to promote enhanced gas response comprises a self-assembled photonic crystal colloidal particles 30 arrays resonator 20 or an inverse opal 32, 33 resonator 20 as illustrated in FIGS. 4A and 4B. These resonators form mesoporous photonic crystal structures. The self-assembled photonic crystal colloidal particle arrays may be formed from colloidal polymeric (e.g. polystyrene, ranging in diameter from 100 to 10,000 nm) particles or colloidal core-shell particles (polystyrene core nanospheres ranging in diameter from 100 to 10,000 nm coated with a sol-gel shell ranging in thickness from 1 to 1000 nm).

In another embodiment, the resonator structure may be a dielectric resonator, made of inorganic materials, polymeric materials, and composite materials, for example. Non-limiting examples of materials of dielectric resonators include polymeric and $SiO_2$ materials, non-limiting examples of inorganic materials include Si, $SiO_2$, $TiO_2$, non-limiting examples of composite materials include Au nanoparticles and polymeric nanoparticles and nanostructures.

In another embodiment, the resonator structure is a metallic resonator, including plasmonic materials. Non-limiting examples of materials include Au, Ag, Al. In another embodiment, this resonator is a hybrid dielectric-metallic resonator where a periodic dielectric structure is formed (e.g. by self-assembly) on a metal plasmonic surface. In another embodiment, this resonator is a resonator made of semiconducting materials (e.g. Si), conducting materials (e.g. Au, Ag, Al), isolating materials (e.g. $SiO_2$, polymers).

In another embodiment, the resonant structure is a long period grating (LPG) written in an optical fiber which when illuminated at resonant optical wavelengths direct light into the glass cladding. The grating consists of a periodic index of refraction variation in the fiber structure. Several LPGs at different resonant wavelengths can be written into the same fiber.

As previously alluded to, in addition to the sensor comprising a resonant structure to promote enhanced gas response versus non-resonant sensors, the resonator further comprises an open-air structure to allow gas to interact with all its regions.

In one embodiment, the structure comprises a gas-impermeable resonator nanostructure material. Non-limiting examples of impermeable resonator nanostructure materials include $SiO_2$, Si, Au, Ag, Al. Gas adsorbs onto impermeable resonator nanostructure with its surface modified with methane-sorption moieties such as metal-organic frameworks, cryptophanes, nanotubes, and others.

In another embodiment, the gas-impermeable resonator structure comprises a structure wherein the evanescent waves exit the resonant structure and interacts with methane-sorption moieties (i.e., gas-permeable materials).

Surface modification of the impermeable resonator nanostructure with the methane-sorption moieties can be performed using known techniques that include liquid-phase deposition and gas-phase deposition. The methane-sorption moieties can be combined with a binder agent that promotes a controlled distribution of the methane-sorption moieties on the surface of the impermeable resonator nanostructure. Non-limiting examples of binder agents are monomers, oligomers and polymers co-deposited with the methane-sorption moieties.

In another embodiment, the structure comprises a gas-permeable resonator nanostructure material that leads to partitioning (absorption) of gases onto vapor-permeable nanostructures. Partitioning (absorption) of gases can occur when the nanostructures are fabricated from materials, such as polymers that are doped with as metal-organic frameworks, cryptophanes, nanotubes, and other methane-sorption moieties. Non-limiting examples of polymers include polymethylmethacrylate, polycarbonate, and silicone. Both types of interactions of gas (such as adsorption and absorption) with the nanostructure lead to the controlled change of resonant conditions of the sensor.

Thus, the mechanism for the selective vapor response of these developed individual sensors involves spatially-controlled interactions of different gases (methane and interferents) with the nanostructures. These localized interactions with specific vapors are expressed in the corresponding regions of the reflectance spectra. This response to diverse vapors is described as multivariable sensing where an individual sensor has several partially or fully independent responses.

In one embodiment, the colorimetric sensors described herein are configured to enable methane detection in upstream oil and gas operations. In other embodiments, the sensor can detect emissions from gate and compressor stations, machine halls, gate valves, pressure relief valves, control valves, connectors, flanges, casing, wellheads and others as well as along pipelines network especially where a pipe meets and forms a connection. In another embodiment, the sensor can be used to detect emissions from oil tanks. In one embodiment, the sensors are attached, using for example an adhesive, in the form of a "sticker" or color-changing tape to the particular equipment to be monitored and the sensors will change color as a result of methane detection. This provides for portable, low cost, localization, and selectivity.

The sensors may be manufactured using known technologies such as, but not limited to conventional photolithography and etching, multilayer nanotransfer printing, imprint embossing and patterning. In one embodiment, the sensors are manufactured on a rigid substrate such as glass, silicon, or others (using for example conventional photolithography and etching). In another embodiment, the sensors are manufactured on a flexible substrate such as plastic sheet made of polycarbonate, polyimide, polyethylene terephthalate, or others. Fabrication methods include batch fabrication of individual sensors or roll-to-roll fabrication.

In another embodiment, the colorimetric sensors can be used in characterizing flare efficiency. It should also be noted that methane leak occurrence is not relegated to just upstream and midstream applications, but is also prevalent in downstream local distribution networks up to and including applications in residential homes and businesses. In yet another embodiment, this sensor could further detect dangerous emissions or leaks from home/business gas generators, water heaters, and cooking appliances.

EXAMPLES

Design of a colorimetric sensor for selective detection of methane was demonstrated using two exemplary multilayer interferometric structures. These sensor structures contained five and ten interferometric layers and each layer had a small extinction coefficient of 0.02 and was sensitive to methane.

More specifically, a design of a methane sensor comprises an interferometric structure with five methane-sensitive layers, whereas a design of a methane sensor comprises an interferometric structure with ten methane-sensitive layers. Each of the layers is 207.1824 nm thick and are separated from each other by an air gap which is 100 nm thick. In this design, the width of the structure is at least 100 times larger than the thickness of the methane-sensitive layers or the air gap. The operating wavelengths for this photonic structure are in the visible spectral range.

An exemplary methane-sensing moiety (i.e. a cryptophane E) was implemented as a part of the resonant structures. Cryptophanes are synthetic organic compounds with enforced cavity of suitable size for molecular guest encapsulation. Their gas selectivity originates from size complementarity and efficient van der Waals interactions with the guest. The internal volume for Cryptophane A is 95 Angstrom$^3$; the internal volume for Cryptophane E is 121 Angstrom$^3$.

Reflectance colorimetric spectra were further determined from optical simulations. These spectral were produced by the constructive and destructive interference of light and resulted in a strong reflectance peak formed at approximately 400 nm. Reflectance spectrum of the five-layer structure is slightly broader that the spectrum of the ten-layer structure.

In addition to cryptophane E and A, other methane-sensing moieties can be incorporated with the multivariable photonic sensors that include metal-organic frameworks, nanotubes, and others.

As previously described, actual modification of the structure with the methane-sensing material is accomplished by known methods. Non-limiting examples include liquid-phase deposition of methane sensing moieties (e.g. cryptophanes, metal-organic frameworks, nanotubes, etc.) onto the gas-impermeable nanostructures or initial incorporation of these methane sensing moieties into the gas-permeable materials followed by fabrication of the photonic nanostructures.

When the sensing colorimetric structure is modified with methane-sensing material, the color of the structure and its reflectance peak changes as a function of methane concentration.

A thin optical filter can be used to select only a particular reflectance range of interest and to observe the change in spectral reflected light intensity over the narrow spectral range. Such sensing film design allows enhancing the visualization of the optical changes upon methane exposures. A change of the reflected light intensity at a single selected wavelength of 430 nm and using a filter with a 20-nm wavelength bandwidth range which is a typical bandwidth of common optical filters.

Figure 5:
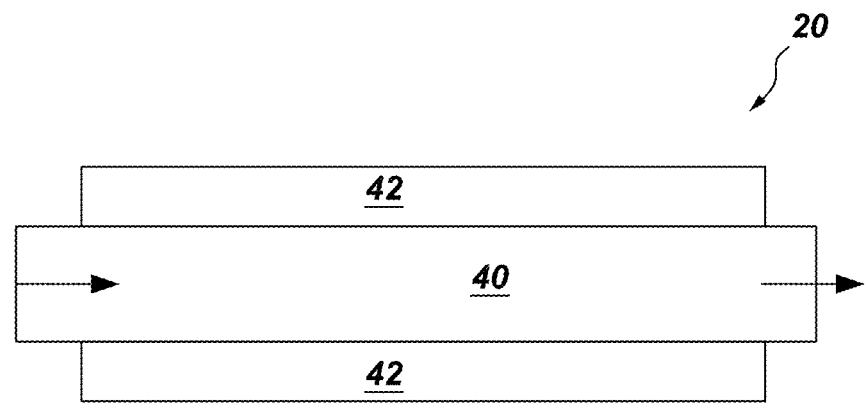
FIG. 5 illustrates an cross-sectional elevation view of a photonic sensor in accordance with an embodiment.

Referring to FIG. 5, a cross-sectional elevation view of an exemplary sensing region 20 comprising a multimode waveguide such as optical fiber 40 and an analyte-permeable cladding 42 such as a plastic silicone cladding is depicted. The cladding of the fiber was impregnated with a chemical reagent such as Nile Red. The impregnation was performed by dissolving the chemical reagent in dichloromethane solvent and immersing the fiber into the solution of Nile Red in dichloromethane. The light from a halogen lamp was launched in to the fiber using an objective. A spatial filter was used to select high order modes that were further detected and spectrally quantified by a spectrograph. In an embodiment, the photonic sensor may allow spectral measurement of high-order modes of reagent-modified fiber cladding of a multimode optical waveguide. In an embodiment, the spectral analysis may be performed within and outside optical features of the reagent. In an embodiment, different components in the analyzed fluid produce desired variation in propagation of high-order modes of the multi-mode optical waveguide. Non-limiting examples of the multimode optical waveguides include optical fibers, planar waveguides, plastic sheets, and glass sheets.

Figure 6:
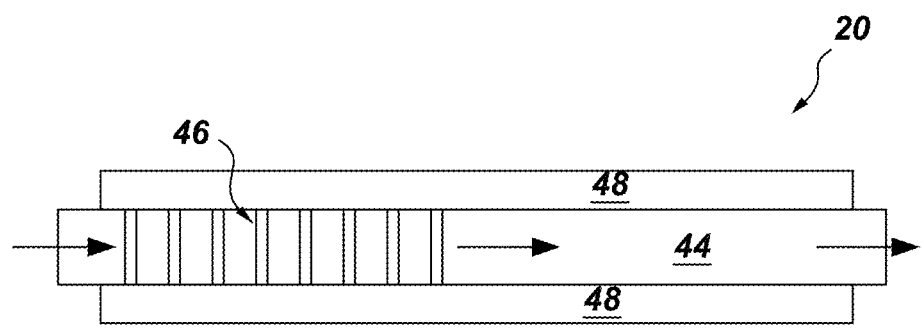
FIG. 6 illustrates an cross-sectional elevation view of a photonic sensor in accordance with another embodiment.

Referring to FIG. 6, a cross-sectional elevation view of an exemplary sensing region 20 that comprises a few-mode waveguide such as optical fiber 44 and a glass cladding 48 is depicted. The few-mode optical fiber had a long period grating (LPG) 46 in its core. The light from a super continuum light source was launched in to the fiber using an objective. Transmitted light was further detected and spectrally quantified by a spectrograph. In an embodiment, the photonic LPG sensor may be operated with super continuum light source. In an embodiment, the photonic LPG sensor may allow spectral measurement of several modes of different "colors". In an embodiment, the spectral analysis of LPG response over spectral range to support more than one mode. In an embodiment, diverse types and locations of environmental effects may produce desired variation in propagation of supported low-order modes of the photonic LPG sensor. In an embodiment, the photonic LPG sensor is selected with the long period grating originally designed and fabricated for the near-infrared application but operated with the light source over the visible or the visible and near-infrared spectral range.

Figure 7:
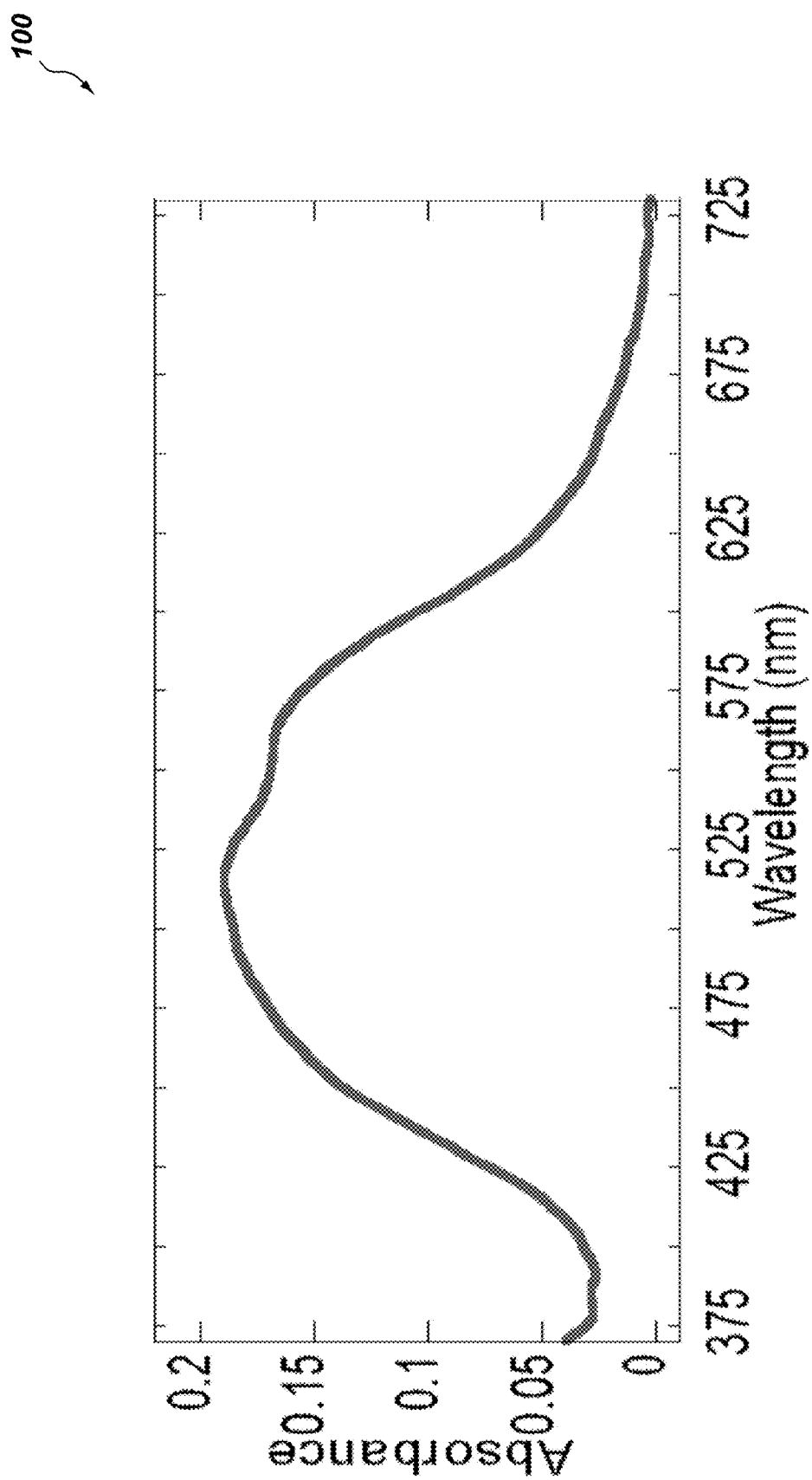
Figure 8:
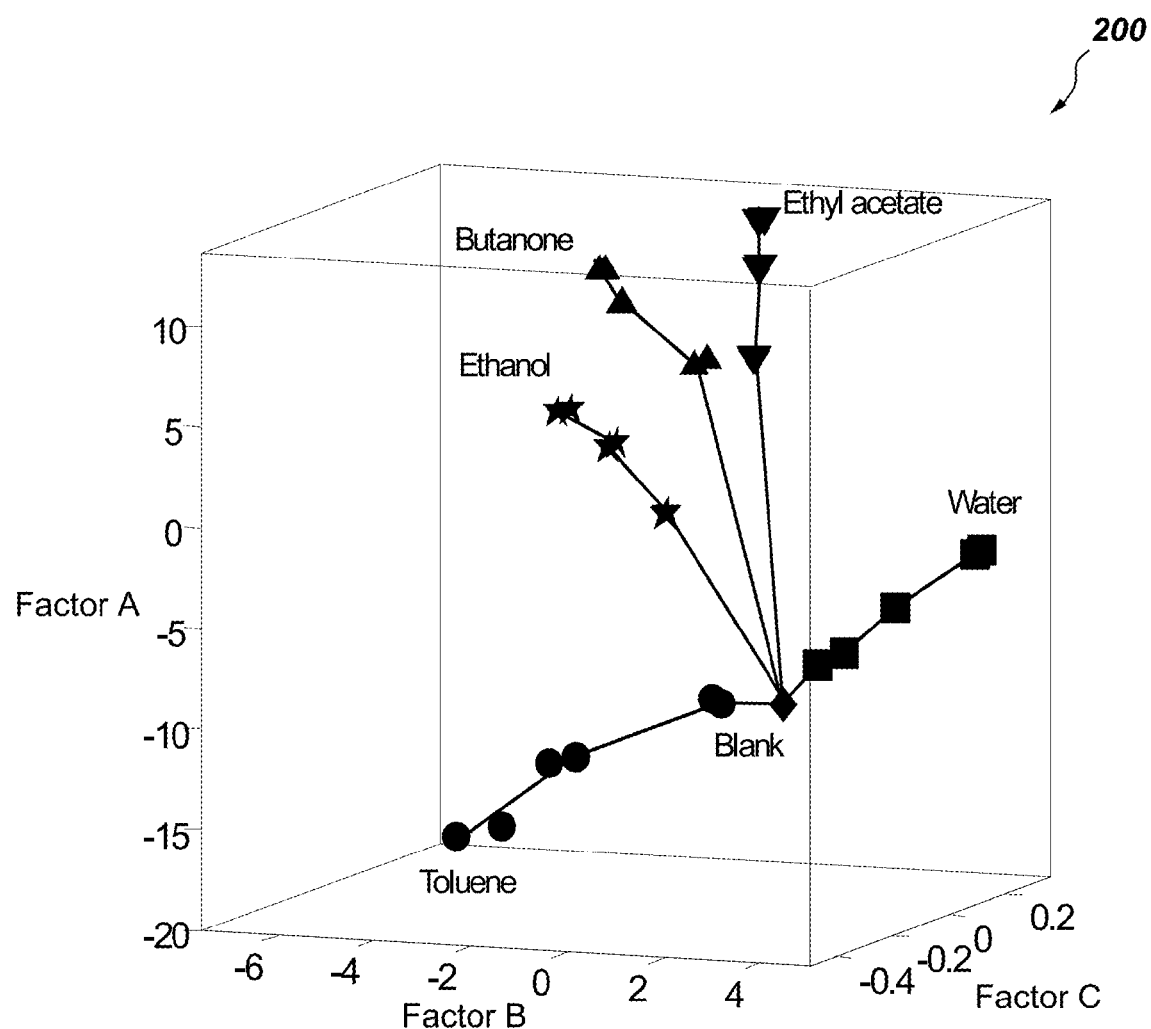

Referring collectively to FIGS. 7-9, depicted are examples of the experimental verification of the photonic sensor operation according to an embodiment such as that illustrated in FIG. 5. Specifically, FIG. 7 depicts transmission spectrum of the optical fiber with the impregnated Nile Red reagent 100. FIG. 8 depicts results of the principal components analysis (PCA) of the spectral responses of the sensor at measured across the spectral response from about 350 nm to about 900 nm 200. This analysis is performed over the spectral region that includes the spectral features of the impregnated reagent and also the cladding that did not contain the response of the reagent. Such broad analysis that combines regions with and without the response of the chemical reagent allows for the generation of multivariable response that discriminated multiple vapors. FIG. 8 illustrates discrimination of five model vapors at their three concentrations each. The tested vapors included water, butanone, ethyl acetate, ethanol, and toluene.

FIGS. 9A-9D illustrate examples of the responses of the developed multivariable sensor at four representative wavelengths such as 400, 570, 590, and 645 nm, FIGS. 9A, 9B, 9C, 9D, respectively. These figures illustrate diverse responses to different vapors such as water, butanone, ethyl acetate, ethanol, and toluene at different wavelengths. This diversity can be summarized as three classes: (i) different relative intensities of responses (e.g., response to ethanol at 400 nm is about the same as response to toluene, whereas response to ethanol at 645 nm is about four times less over the response to toluene); (ii) opposite directions of responses (e.g., response to ethanol at 400 nm is opposite to response to toluene, whereas response to ethanol at 570 nm is same as response to toluene); and (iii) different dynamic responses (e.g., the response to toluene at 400, 570, and 590 nm).

Figure 10:
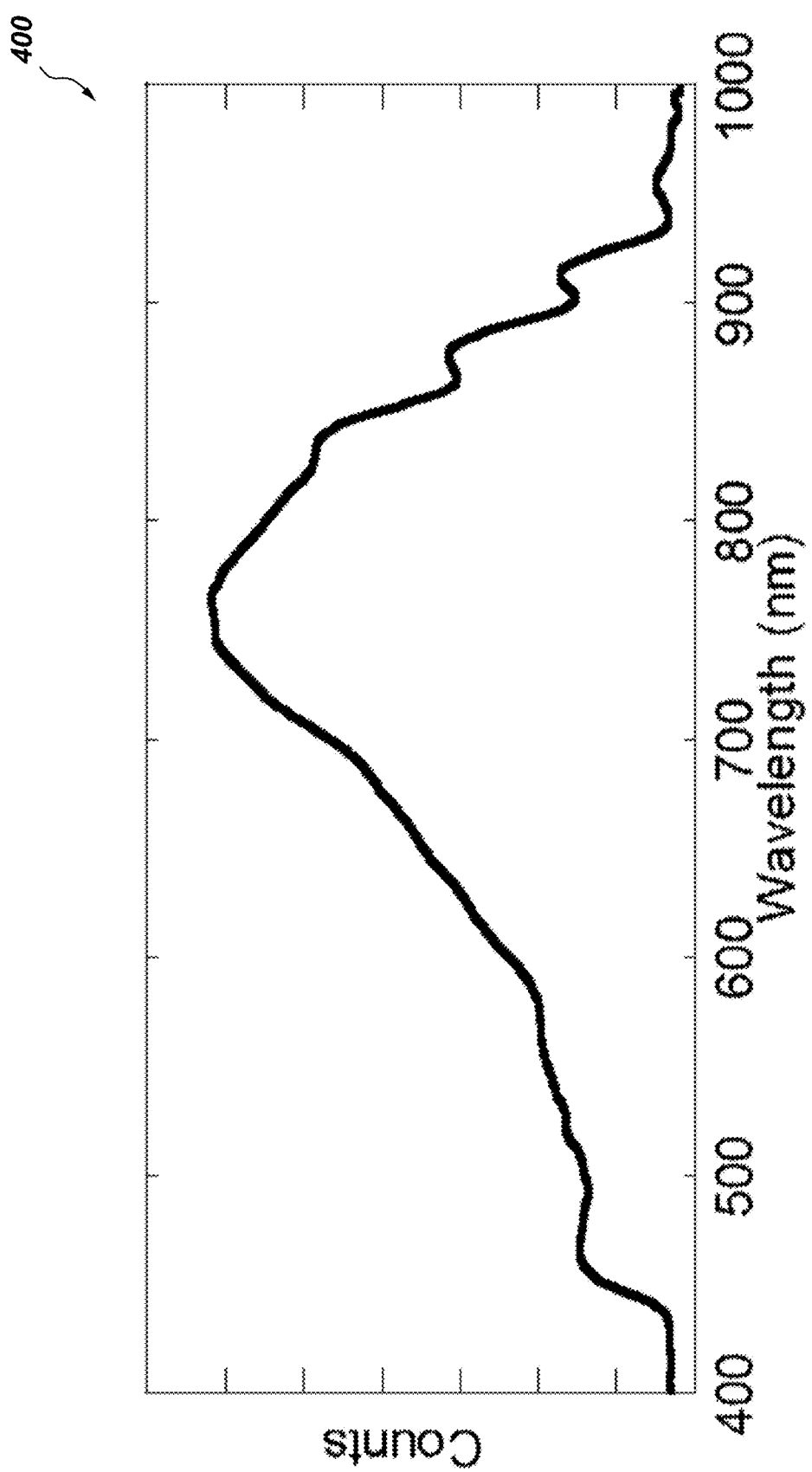
FIGS. 10-12 collectively illustrate experimental verification of the operation of an embodiment of the photonic sensor from FIG. 6, and specifically.
Figure 11:
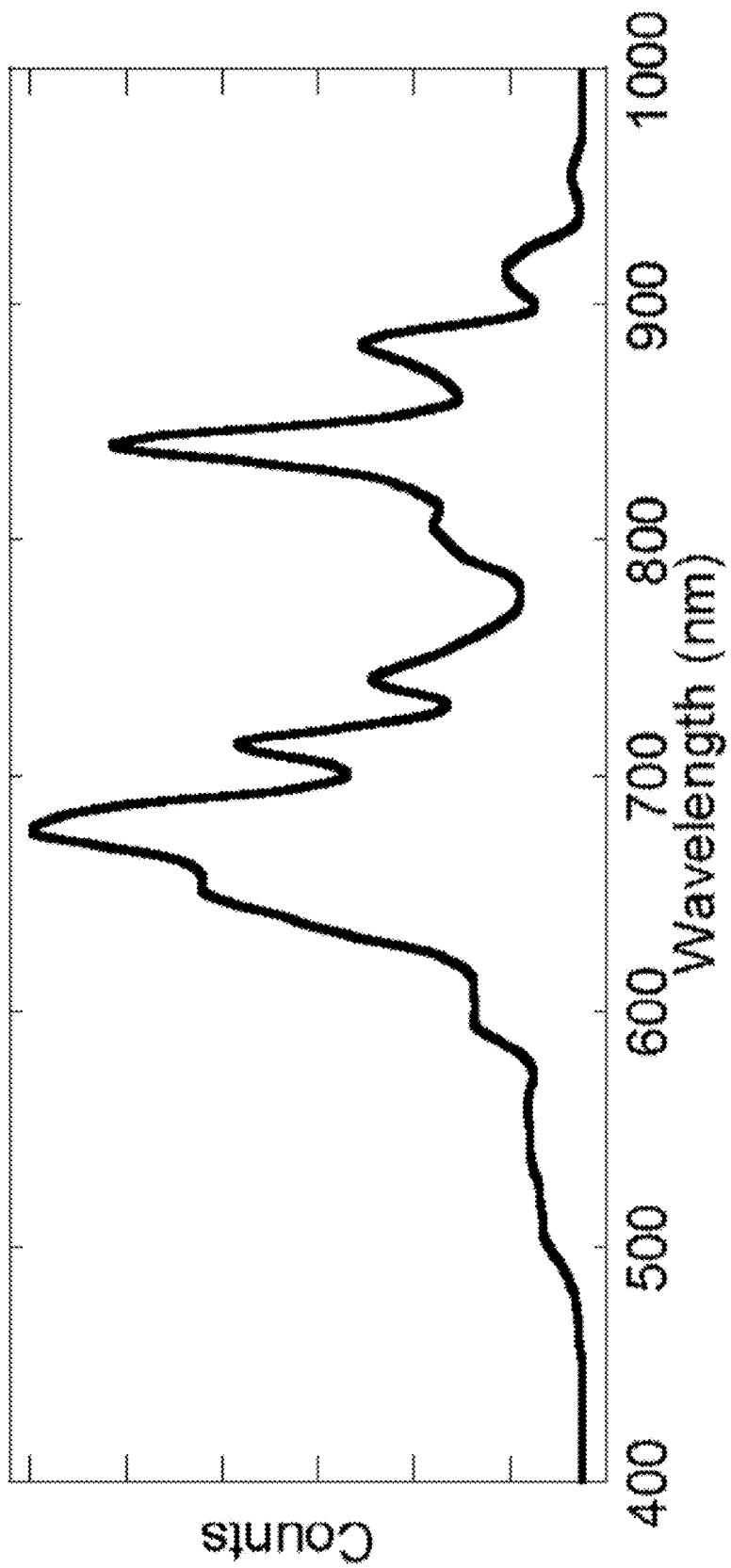
Figure 12:
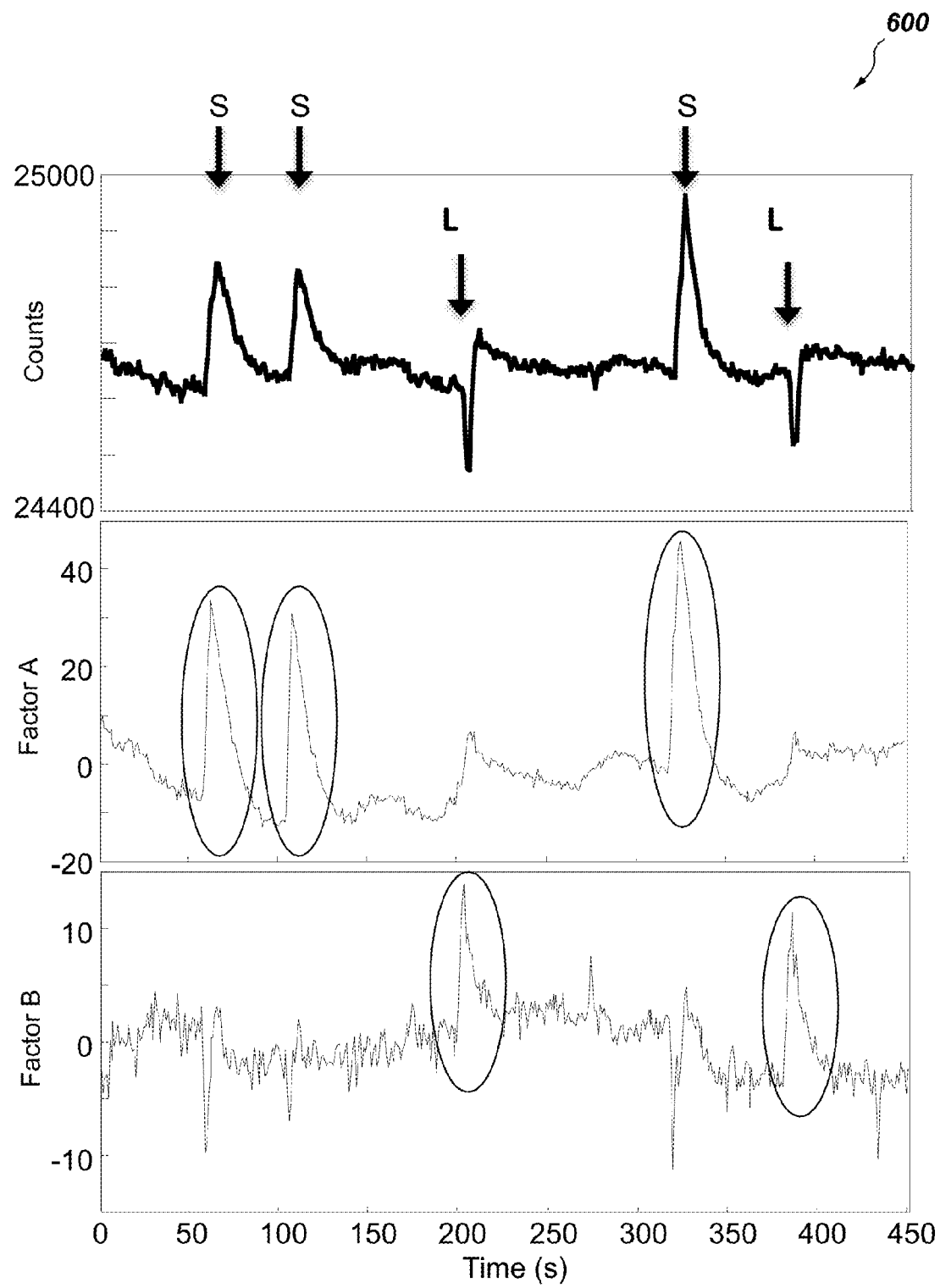

Referring collectively to FIGS. 10-12, depicted are examples of the experimental verification of the photonic sensor operation according to an embodiment such as that illustrated in FIG. 6. Specifically, FIG. 10 depicts emission spectrum of the super continuum light source 400. FIG. 11 depicts emission spectrum of the super continuum light source as transmitted thought the optical fiber and the long period grating on the sensing region of the fiber. FIG. 12 demonstrates results of measurements of thermal effects on the optical fiber within the sensing region (S) that is the long period grating and the fiber link (L) 600. The top graph of FIG. 12 depicted results of detection at a single wavelength such as 885 nm. This result depicts that thermal response effects are pronounced from sensing region (S) and the fiber link (L) but in different directions. The spectral response was analyzed using PCA and its results are presented in the middle and low graphs in FIG. 12. The middle graph depicts the discrimination between numerous effects and the thermal effect on the sensing region as depicted by the three replicate measurements. The bottom graph depicts the discrimination between numerous effects and the thermal effect on the fiber link region as depicted by the two replicate measurements.

Figure 13A:
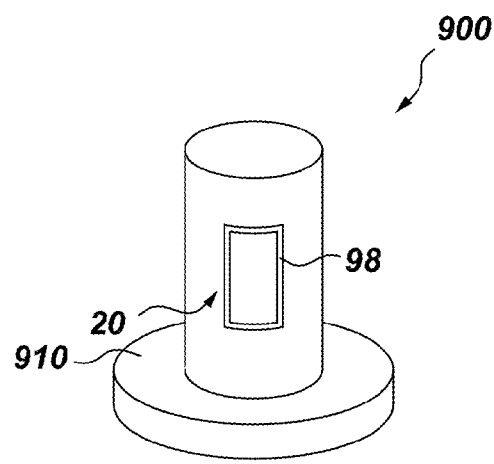
FIGS. 13A-13C illustrate exemplary applications of sensors to an exemplary infrastructure component, such as a flange, using an adhesive (FIG. 13A), a plastic strap (FIG. 13B), and a clamp (FIG. 13C) in accordance with various embodiments.
Figure 13B:
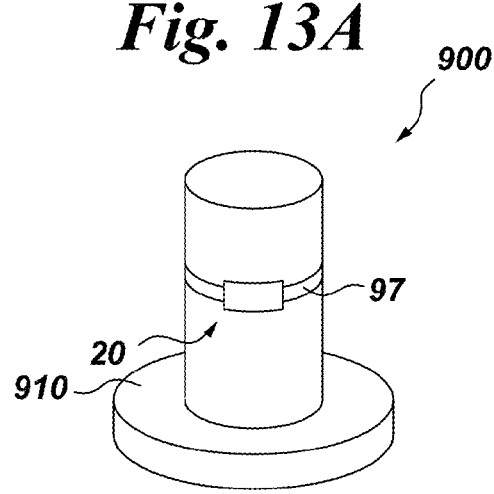
Figure 13C:
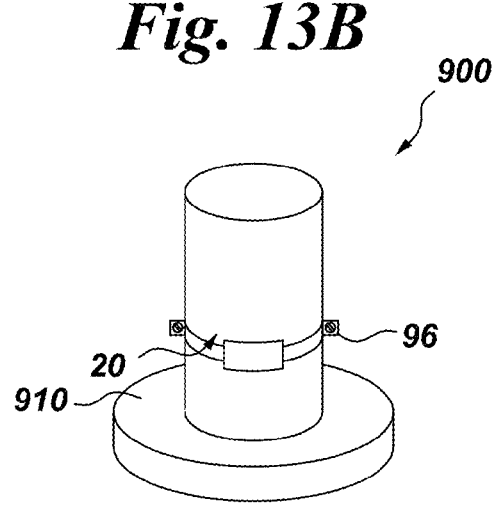

Mounting methods of the fabricated sensors include clamping (for example using conventional tube clamps or connector clamps) or using an adhesive, for example, using an outdoor mounting tape (Scotch Brand, 3M, Saint Paul, Minn. or Loctite Power Grab Mounting Tape, Loctite, Düsseldorf, Germany). Such outdoor mounting tapes are waterproof and have high resistance to UV light, and aging. They can be applied on metal, wood, stone, glass and plastic surfaces. The application of the tape with the sensor should be above 10 degrees C. The service temperature range is typically from −40 degrees C. to 120 degrees C. For example, sensors that are manufactured on a rigid substrate may be mounted using clamping methods, whereas sensors that are manufactured on a flexible substrate may be mounted using clamping or adhesive. In another example, sensors that are manufactured on a rigid or flexible substrate may be mounted using a plastic strap. Examples of application of the sensors 20 to an exemplary infrastructure component such as a pipe 900 having a flange 910 using an adhesive 98, a plastic strap 91, and a clamp 96 are illustrated in FIGS. 13A, 13B, and 13C, respectively.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fluid sensor comprising:
   a rigid or flexible substrate;
   a plurality of fluid sensitive interferometric nanostructure layers manufactured on the substrate;
   wherein the plurality of fluid sensitive interferometric nanostructure layers includes alternating high and low porosity layers;
   wherein the fluid sensor is an open-fluid resonant structure that allows a fluid to interact with all regions of the fluid sensor; and
   wherein the open-fluid resonant structure comprises a tree-like structure having a vertical element connected to a plurality of horizontal lamella, wherein the vertical element is connected to each of the plurality of horizontal lamella in the middle.

2. The fluid sensor of claim 1, where a quantity of the plurality of interferometric nanostructure layers is between four and 11.

3. The fluid sensor of claim 1, wherein the fluid sensitive interferometric nanostructure layers comprise a fluid sensing moiety comprising one of: Cryptophane, metal-organic framework, nanotubes, nanowires, and nanomaterials.

4. The fluid sensor of claim 1, wherein each of the plurality of layers has an extinction coefficient of about 0.02.

5. The fluid sensor of claim 1, wherein the open-fluid resonant structure is arranged to add diffraction effects to the sensor response.

6. The fluid sensor of claim 1, wherein the plurality of fluid sensitive interferometric nanostructure layers are configured to provide a selective response to one component of the fluid, wherein the fluid comprises a plurality of components.

7. The fluid sensor of claim 1, wherein the plurality of fluid sensitive interferometric nanostructure layers is partitioned into a plurality of narrow multilayer sections with spacing therebetween.

8. The fluid sensor of claim 1, wherein the fluid sensitive interferometric nanostructure layers comprise methanesorption moieties combined with a binder agent.

9. The fluid sensor of claim 8, wherein the methanesorption moieties include cryptophanes and the binder agent includes at least one of monomers, oligomers and polymers.

10. The fluid sensor of claim 1, wherein the open-fluid resonant structure includes long period grating written in an optical fiber.

11. The fluid sensor of claim 1, wherein the thickness of fluid sensitive interferometric nanostructure layers is in the range from 10 nm to 10,000 nm.

12. The fluid sensor of claim 1, wherein the plurality of fluid sensitive interferometric nanostructure layers includes at least two types of materials having different refractive indices.

13. The fluid sensor of claim 12, wherein the refractive indices are in the range from about 1.01 to about 5.

14. The fluid sensor of claim 1, wherein the flexible substrate includes a plastic sheet made of at least one of polycarbonate, polyimide, polyethylene terephthalate.

15. The fluid sensor of claim 1, wherein the rigid substrate is made up of glass or silicone.

16. A photonic sensor system comprising:
   a photodetector;
   a signal processor communicatively coupled to the photodetector;
   a sensor structure is an open-fluid resonant structure configured to provide fluid-response selectivity, spatially distribute light, and to receive light from a light source and convey light to the photodetector;
   wherein the sensor structure includes a plurality of fluid sensitive interferometric nanostructure layers manufactured on a substrate;
   wherein the plurality of fluid sensitive interferometric nanostructure layers includes alternating high and low porosity layers; and
   wherein the open-fluid resonant structure comprises a tree-like structure having a vertical element connected to a plurality of horizontal lamella, wherein the vertical element is connected to each of the plurality of horizontal lamella in the middle.

17. The photonic sensor system of claim 16, wherein the photonic sensor system is configured to selectively measure a plurality of components in a fluid.

18. The photonic sensor system of claim 16, wherein the sensor structure comprises one of: a structural color structure, a resonant structure, a metallic structure, a dielectric structure, a waveguide structure, single-ring resonator structure, multi-ring resonator structure, whispering-gallery wave structure, and a grating structure.

19. The photonic sensor system of claim 16, wherein the sensor structure comprises a metamaterial sensing structure.

20. The photonic sensor system of claim 16, wherein the sensor structure incorporates one of: an organic sensing material, an inorganic sensing material, a biological sensing material, a plasmonic sensing material, a composite sensing material, and a nanocomposite sensing material.

21. The photonic sensor system of claim 16, wherein the sensor structure is configured to be affected by the fluid.

22. A method of selective measurement of a plurality of components in a fluid in a process area comprising:
   exposing a sensing structure to the fluid, wherein the sensor structure is an open-fluid resonant structure;
   interrogating the sensing structure with light from a light source,
   wherein the light source is outside the process area and the light has a set of predetermined properties; measuring a change in optical properties of the sensing structure; correlating the measured change to a stored value;
   providing quantitative values of levels of the plurality of components in the fluid;
   wherein the sensing structure includes a plurality of fluid sensitive interferometric nanostructure layers manufactured on a substrate; wherein the plurality of fluid sensitive interferometric nanostructure layers includes alternating high and low porosity layers; and
   wherein the open-fluid resonant structure comprises a tree-like structure having a vertical element connected to a plurality of horizontal lamella, wherein the vertical element is connected to each of the plurality of horizontal lamella in the middle.

23. The method of claim 22, further comprising rejecting unwanted interferents between components of interest in the fluid and interferents.

24. The method of claim 23, wherein the interferents comprise a group of gaseous interferents.

25. The method of claim 23, wherein the interferents comprise at least one of moisture, pressure, and temperature.

26. The method of claim 22, further comprising correcting for aging of the sensing structure.

27. The method of claim 22, further comprising expanding a dynamic range of measurements by one of: spectral multiplexing, polarization multiplexing, and time-domain multiplexing.

* * * * *